United States Patent
Horta et al.

(10) Patent No.: US 10,835,262 B2
(45) Date of Patent: Nov. 17, 2020

(54) TIBIAL POSTERIOR SLOPE ALIGNMENT GUIDE

(71) Applicant: Howmedica Osteonics Corp., Mahwah, NJ (US)

(72) Inventors: Luis F. Horta, Bogota, NJ (US); Debaditya Roychowdhury, Mahwah, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 16/204,491

(22) Filed: Nov. 29, 2018

(65) Prior Publication Data

US 2019/0167275 A1 Jun. 6, 2019

Related U.S. Application Data

(60) Provisional application No. 62/595,220, filed on Dec. 6, 2017.

(51) Int. Cl.
*A61B 17/15* (2006.01)
*A61B 17/56* (2006.01)

(52) U.S. Cl.
CPC .......... *A61B 17/157* (2013.01); *A61B 17/154* (2013.01); *A61B 17/56* (2013.01); *A61B 2017/564* (2013.01)

(58) Field of Classification Search
CPC ..... A61B 17/15; A61B 17/154; A61B 17/157; A61B 17/164; A61B 17/56; A61B 2017/564; A61B 17/72
See application file for complete search history.

(56) References Cited

U.S. PATENT DOCUMENTS

| | | | |
|---|---|---|---|
| 4,841,975 A | 6/1989 | Woolson | |
| 4,952,213 A * | 8/1990 | Bowman | A61B 17/157 606/62 |
| 5,002,545 A | 3/1991 | Whiteside et al. | |
| 5,122,144 A | 6/1992 | Bert et al. | |
| 5,234,433 A | 8/1993 | Bert et al. | |
| 5,250,050 A | 10/1993 | Poggie et al. | |
| 5,306,276 A | 4/1994 | Johnson et al. | |
| 5,342,368 A | 8/1994 | Petersen | |
| 5,431,656 A | 7/1995 | Clift, Jr. et al. | |
| 5,445,640 A | 8/1995 | Johnson et al. | |
| 5,451,228 A | 9/1995 | Johnson et al. | |

(Continued)

*Primary Examiner* — Larry E Waggle, Jr.
(74) *Attorney, Agent, or Firm* — Lerner, David, Littenberg, Krumholz & Mentlik, LLP

(57) ABSTRACT

A resection guide system for resecting an end of bone includes an anchoring block having an elongate shaft and an opening extending through the anchoring block at one end thereof. The opening is sized to receive a rod therein and defines an axis. A translation member includes a housing and a shaft extending therefrom. The housing is engageable to the shaft of the anchoring block in a first configuration in which the shaft of the translation member is oriented at a first angle relative to the axis of the opening and a second configuration in which the shaft of the translation member is oriented at a second angle relative to the axis of the opening. A resection guide assembly connects to the shaft of the translation member and has a resection guide surface adapted to guide a cutting instrument along a plane defined by the resection guide surface.

18 Claims, 5 Drawing Sheets

(56) References Cited

U.S. PATENT DOCUMENTS

| | | | |
|---|---|---|---|
| 5,578,039 A * | 11/1996 | Vendrely | A61B 17/157 606/88 |
| 5,601,563 A | 2/1997 | Burke et al. | |
| 5,628,749 A | 5/1997 | Vendrely et al. | |
| 5,628,750 A | 5/1997 | Whitlock et al. | |
| 5,667,511 A | 9/1997 | Vendrely et al. | |
| 5,681,316 A * | 10/1997 | DeOrio | A61B 17/157 606/87 |
| 5,897,559 A | 4/1999 | Masini | |
| 5,916,219 A | 6/1999 | Matsuno et al. | |
| 6,090,114 A | 7/2000 | Matsuno et al. | |
| 6,258,095 B1 | 7/2001 | Lombardo et al. | |
| 6,740,092 B2 | 5/2004 | Lombardo et al. | |
| 7,033,361 B2 | 4/2006 | Collazo | |
| 7,618,420 B2 * | 11/2009 | Collazo | A61B 17/157 606/86 R |
| 7,618,422 B2 | 11/2009 | Goodwin | |
| 7,927,336 B2 | 4/2011 | Rasmussen | |
| 7,931,690 B1 | 4/2011 | Bonutti | |
| 8,118,811 B2 | 2/2012 | Coon et al. | |
| 8,128,630 B2 | 3/2012 | Goodwin | |
| 8,337,498 B2 | 12/2012 | Rasmussen | |
| 8,758,354 B2 | 6/2014 | Habegger et al. | |
| 8,876,831 B2 | 11/2014 | Rasmussen | |
| 8,979,847 B2 | 3/2015 | Belcher et al. | |
| 9,028,501 B2 | 5/2015 | Thomas et al. | |
| 9,095,356 B2 | 8/2015 | Thomas et al. | |
| 9,149,284 B2 | 10/2015 | Rasmussen | |
| 2001/0001121 A1 | 5/2001 | Lombardo et al. | |
| 2004/0153066 A1 | 8/2004 | Coon et al. | |
| 2006/0142774 A1 | 6/2006 | Metzger | |
| 2006/0184173 A1 | 8/2006 | Collazo | |
| 2006/0189998 A1 | 8/2006 | Rasmussen | |
| 2006/0200158 A1 * | 9/2006 | Farling | A61B 17/155 606/87 |
| 2007/0233138 A1 | 10/2007 | Figueroa et al. | |
| 2008/0183178 A1 | 7/2008 | Collazo | |
| 2008/0306484 A1 | 12/2008 | Coon et al. | |
| 2009/0043309 A1 | 2/2009 | Rasmussen | |
| 2009/0043310 A1 | 2/2009 | Rasmussen | |
| 2010/0004702 A1 | 1/2010 | Goodwin | |
| 2010/0042103 A1 | 2/2010 | Rasmussen | |
| 2010/0094300 A1 | 4/2010 | Coon et al. | |
| 2011/0015636 A1 | 1/2011 | Katrana et al. | |
| 2011/0130762 A1 | 6/2011 | Metzger et al. | |
| 2012/0101504 A1 | 4/2012 | Habegger et al. | |
| 2012/0245589 A1 | 9/2012 | Fisher et al. | |
| 2012/0310246 A1 | 12/2012 | Belcher et al. | |
| 2013/0325019 A1 | 12/2013 | Thomas et al. | |
| 2013/0325136 A1 | 12/2013 | Thomas et al. | |
| 2014/0012262 A1 | 1/2014 | Rasmussen | |
| 2014/0180294 A1 | 6/2014 | Collins | |
| 2014/0243990 A1 | 8/2014 | Collazo et al. | |
| 2014/0257289 A1 | 9/2014 | Kecman et al. | |
| 2014/0324054 A1 | 10/2014 | Dmuschewsky et al. | |
| 2015/0157472 A1 | 6/2015 | Belcher et al. | |
| 2015/0173781 A1 | 6/2015 | Metzger et al. | |
| 2015/0289884 A1 | 10/2015 | Fisher et al. | |
| 2015/0359546 A1 | 12/2015 | Thomas | |
| 2016/0022278 A1 | 1/2016 | Rasmussen | |
| 2016/0045205 A1 | 2/2016 | Metzger et al. | |

* cited by examiner

TIBIAL POSTERIOR SLOPE ALIGNMENT GUIDE

CROSS-REFERENCE TO RELATED APPLICATIONS

This application claims the benefit of the filing date of U.S. Provisional Patent Application No. 62/595,220, filed Dec. 6, 2017, the disclosure of which is hereby incorporated herein by reference.

BACKGROUND OF THE INVENTION

Total knee arthroplasty (TKA) or total knee replacement is a common orthopedic procedure in which damaged or diseased articular cartilage and/or bone of the knee is replaced with prosthetic components. Prior to implanting such components, a surgeon generally resects a portion of the patient's native bone in order to shape the bone to receive the prosthetic components. For example, a surgeon might make one or more planar cuts at a distal end of a femur and proximal end of a tibia so that corresponding surfaces of femoral and tibial prosthetic components can be respectively attached thereto.

Each individual cut of a section of bone is carefully made. Once native bone is resected from a joint, it is gone forever. In addition, the amount of bone resected and the final geometries of the resected bone significantly influence the fit and alignment of the prosthetic components. Improper fit and/or alignment can result in instability of the joint, increased risk of bone fracture and component failure, pain, and reduced range of motion.

Multiple resection philosophies/techniques have emerged over the years to help ensure proper fit and alignment of the prosthetic components comprising the artificial joint. For example, mechanical axis alignment, anatomic axis alignment, gap balancing, measured resection, anterior referencing, and posterior referencing are some of the various techniques/philosophies that have been widely adopted for forming bone in a TKA procedure.

Surgeons often prefer one technique/philosophy over another. To accommodate surgeon preference, numerous instrument sets have been made available to help guide each cut of a femur and tibia in accordance with a particular technique/philosophy often to the exclusion of other techniques/philosophies. These instruments typically guide a saw blade or other cutting tool to cut a bone at a particular angle and to remove a particular amount of bone. Although, a certain amount of preoperative planning using radiographic images helps a surgeon plan each cut of a joint surface, the actual amount of bone removed and the angle of each cut is often unknown until the TKA procedure is well under way. As such, many instrument sets provide instruments with complicated mechanisms or duplicate instruments that are designed to remove different amounts of bone and guide a cut at different relative angles, as needed during the procedure.

The result is that a single manufacturer may provide different sets of instruments for performing the various resection philosophies/techniques with each set including a large quantity of instruments and instruments with complex, failure prone mechanisms. Prior to a TKA procedure, a surgeon or healthcare facility may order a set of instruments for performing the procedure according to the surgeon's preferred technique/philosophy. These instruments may be stored, sterilized, packaged, and shipped by the manufacturer to the healthcare facility in which the procedure is to take place. In some instances, the instruments may be stored and sterilized at the healthcare facility itself.

The demands of manufacturing, storing, maintaining, sterilizing, packaging, shipping and tracking such a diverse, complicated and large quantity of instruments can be expensive, particularly in a world that is increasingly demanding cheaper surgical procedures. For example, a set of instruments for performing a TKA procedure may cost about 40,000 USD to manufacture. These instruments may then be placed into circulation and are often only provided to a few surgeons who subscribe to the technique/philosophy for which the instrument set was designed. While in circulation, these instruments must be stored, repaired, sterilized, packaged and shipped numerous times over, thereby contributing to the overall costs of the instruments. The more complicated the instrument and the more instruments provided in each set, the greater the life-cycle costs become, which may reflect back to the cost of the TKA procedure.

Therefore, further improved instruments for use in TKA procedures are desired.

BRIEF SUMMARY OF THE INVENTION

The present disclosure describes devices, systems, and methods for performing a proximal tibial resection in a TKA procedure. In particular, a system is described that includes an intramedullary ("IM") jig and a resection guide assembly. The IM jig includes an anchoring block and an anterior/posterior ("A/P") translation member. The IM jig is configured to connect to an IM rod extending from a proximal tibia via an opening in the anchoring block. Moreover, the A/P translation member is configured to connect to the anchoring block in a first or second configuration such that in a first configuration, a resection guide surface of the resection guide assembly is positioned in a first orientation relative to a tibia, and in the second configuration, the resection guide surface of the resection guide assembly is positioned in a second orientation relative to the tibia. Such orientations allow a cutting device to cut the proximal tibia along the resection guide surface to form a resected surface with a predefined posterior slope. The first configuration is achieved by inserting a shaft of the guide block through a first end of a housing of the A/P member, while the second configuration is achieved by inserting the shaft of the guide block through a second end of the housing of the A/P member.

In one aspect of the present disclosure, a resection guide system for resecting an end of bone includes an anchoring block that has an elongate shaft and an opening extending through the anchoring block at one end thereof. The opening is sized to receive an intramedullary rod therein. The opening defines a longitudinal axis. The system also includes a translation member that has a housing and a shaft extending therefrom. The housing of the translation member is engageable to the shaft of the anchoring block in a first configuration in which the shaft of the translation member is oriented at a first angle relative to the longitudinal axis of the opening and a second configuration in which the shaft of the translation member is oriented at a second angle relative to the longitudinal axis of the opening. The system further includes a resection guide assembly connected to the shaft of the translation member and has a resection guide surface adapted to guide a cutting instrument along a plane defined by the resection guide surface.

Additionally, the the shaft of the anchoring block may have a shaft axis that intersects the longitudinal axis of the opening at an obtuse angle. The housing of the translation member may have an opening extending therethrough from a first end to a second end thereof. The opening of the housing may be configured to receive the shaft of the anchoring block. The anchoring block may include a head at an end of shaft. The head may have a cross-sectional dimension greater than the shaft and the opening may extend through the head. In a first configuration, the shaft of the anchoring block may through the opening of the housing so that the first end of the housing faces the head of the anchoring block, and in the second configuration, the shaft of the anchoring block may extend through the opening of the translation member so that the second end of the housing faces the head of the anchoring block.

Continuing with this aspect, the shaft of the translation member may be canted relative to the housing. Also, in the first configuration, the shaft of the anchoring block may be received in the opening of the housing so that the shaft of the translation member is canted toward the head of the anchoring block, and in the second configuration the shaft of the anchoring block may be received in the opening of the housing so that the shaft of the translation member is canted away from the head of the anchoring block. The first angle may 0 degrees such that the longitudinal axis is parallel to the shaft of the translation member, and the second angle is 3 degrees. The plane defined by the resection guide surface may perpendicular to the shaft axis of the translation member.

In another aspect of the disclosure, a resection guide system for resecting an end of a tibia includes an anchoring block that has a shaft and opening extending through the shaft at an end thereof. The opening is configured to receive an IM rod extending from the tibia. The system also includes a translation member that has a housing and a shaft extending from the housing. The system further includes a resection guide assembly that has a resection guide surface. The resection guide assembly is connectable to the shaft of the translation member. The housing of the translation member is configured to connect to the anchoring block in a first configuration such that the resection guide surface of the resection guide assembly is positioned in a first orientation relative to the tibia when the IM rod is received within the opening and in a second configuration such that the resection guide surface of the resection guide assembly is positioned in a second orientation relative to the tibia.

Additionally, in the first configuration, a first end of the housing may face the anchoring block, and in the second configuration a second end of the housing may face the anchoring block. The housing may define an opening extending therethrough from the first end to the second end thereof. The opening may define a housing axis and may be configured to receive the shaft of the anchoring block. The shaft of the translation member may be canted relative to the housing such that a shaft axis of the translation member intersects the housing axis at an oblique angle. The anchoring block may include a head at an end thereof. The head may have a cross-sectional dimension greater than the shaft and the opening may extend through the head. The shaft of the anchoring block may be canted relative to the head such that a shaft axis of the anchoring block intersects a longitudinal axis of the opening of the head at an oblique angle. The resection guide surface may be perpendicular to the shaft of the translation member when the resection guide assembly is connected thereto.

In a further aspect of the disclosure, a method of resecting a proximal tibia includes mounting an anchoring block onto an IM rod extending from the proximal tibia, and selecting one of a first and second posterior slope angle for application to the proximal tibia. If the first posterior slope angle is selected, mounting a translation member carrying a resection guide assembly is mounted to the anchoring block in a first configuration such that a shaft of the anchoring block engages a housing of the translation member and a first end of the housing faces the tibia, and the resection guide assembly having a resection guide surface disposed in a first orientation relative to the tibia. If the second posterior slope angle is selected, the translation member carrying the resection guide assembly to the anchoring block is mounted in a second configuration such that the shaft engages the housing and a second end of the housing faces the tibia, and the resection guide surface is disposed in a second orientation relative to the tibia. The method also includes resecting the tibia along a resection guide surface of the resection guide assembly.

Additionally, in the second configuration, a shaft of the translation member may be canted away from the tibia, and the resection guide assembly may be connected to the shaft of the translation member. Also, mounting the anchoring block to the IM rod may include inserting the IM rod into an opening extending through a head of the anchoring block. Moreover, mounting the translation member to the anchoring block in the first configuration may include inserting a shaft of the anchoring block through an opening in the housing of the translation member from the first end of the housing to the second end of the housing. Furthermore, mounting the translation member to the anchoring block in the second configuration may include inserting the shaft of the anchoring block through the opening in the housing of the translation member from the second end of the housing to the first end of the housing.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face and the term "posterior" means toward the back of the body. Also, as used herein, the terms "about," "generally" and "substantially" are intended to mean that slight deviations from absolute are included within the scope of the term so modified.

FIGS. 1-5 depict a tibial resection system 10 according to an embodiment of the present disclosure. Tibial resection system 10 includes an IM jig 12 and a resection guide assembly 40. IM jig 12 connects to an IM rod (see FIG. 5) extending from a tibia and can be configured to orient a resection guide surface 44 of resection guide assembly 40 connected to IM jig 12 in one of a plurality of different orientations relative to a tibia so as to allow an operator to apply a desired posterior slope to a resected proximal tibia, as is described in more detail below.

Figure 2A:
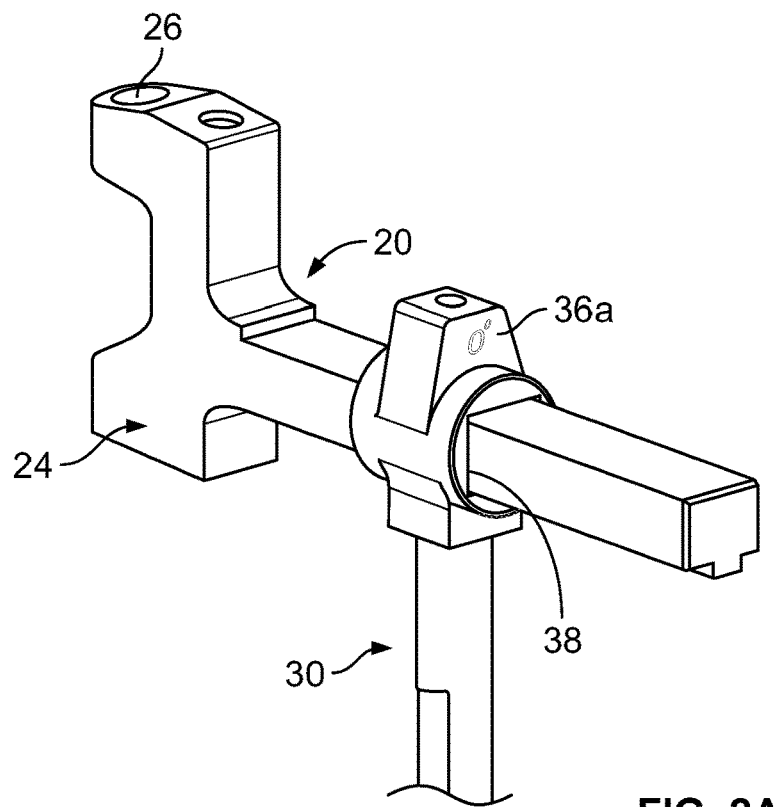
FIG. 2A is a partial perspective view of the IM jig of FIG. 1 in a first configuration.
Figure 2B:
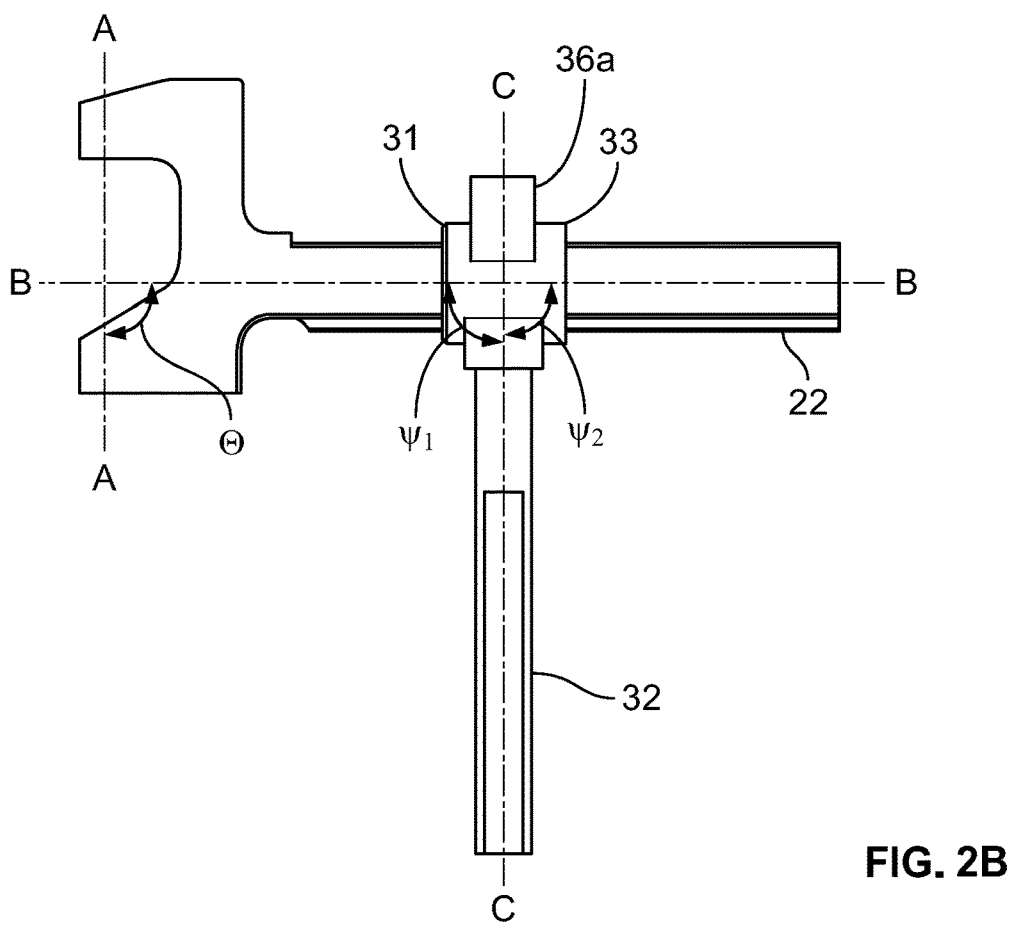
FIG. 2B is an elevational view of the IM jig of FIG. 1 in the first configuration.

IM jig 12 includes an anchoring block 20 and an A/P translation member 30. Anchoring block 20 includes a shaft 22 and a block head 24 at an end of shaft 22. An opening 26 extends through block head 24 and is sized to receive an IM rod. Block head 24 includes a notch 25 that intersects opening 26 so that an IM rod extending through opening 26 can be observed by the operator. Opening 26 defines an axis A-A that intersects a longitudinal axis B-B of the shaft at an obtuse angle θ, as best shown in FIGS. 2B and 3B. In the particular embodiment depicted, the block angle θ is 91.5 degrees, or 1.5 degrees beyond perpendicular. However, as is described below, block angle θ can be one of a number of different angles depending on the desired angle of resection.

IM jig 12 is advantageous in that it comprises few components. Thus, because there are few component connections between IM rod 50 and resection guide 42, there is little accuracy loss due to component tolerances. Therefore, IM jig 12 provides a highly accurate posterior slope angle.

A/P translation member 30 includes a shaft 32 and a housing or head 34 at an end of shaft 32. Housing 34 includes a first end 31, a second end 33, and an opening 38 (see FIG. 4) extending through the first and second ends 31, 33. Opening 38 is configured to receive shaft 22 of anchoring block 20. In this regard, opening 38 may be polygonal in correspondence with a polygonal shape of shaft 22. Such polygonal shape helps prevent rotation of shaft within housing. However, other shapes are contemplated. Opening 38 also defines a longitudinal axis B-B that intersects an axis C-C of shaft 32, as shown in FIGS. 2B and 3B. Such intersection forms a first oblique angle $\Psi_1$ and a second oblique angle $\Psi_2$. In the particular embodiment depicted, first member angle $\Psi_1$ is 88.5 degrees, or −1.5 degrees beyond perpendicular, and second member angle $\Psi_2$ is 91.5 degrees, or 1.5 degrees beyond perpendicular. In this regard, shaft 32 is canted relative to housing 34. However, as is described below, member angles $\Psi_1$, $\Psi_2$ can differ from those mentioned above depending on the desired angle of resection.

A/P translation member 30 is also slidable in an A/P direction along shaft 22 when shaft 22 is received in opening 38. In some embodiments, shaft 22 may include detents (not shown) at equally spaced intervals along its length, and housing 34 may contain a spring biased ball bearing (not shown) for engagement with such detents. Such ball-detent mechanism may help prevent unintended movement of A/P translation member 30 relative to block head 24.

Figure 1:
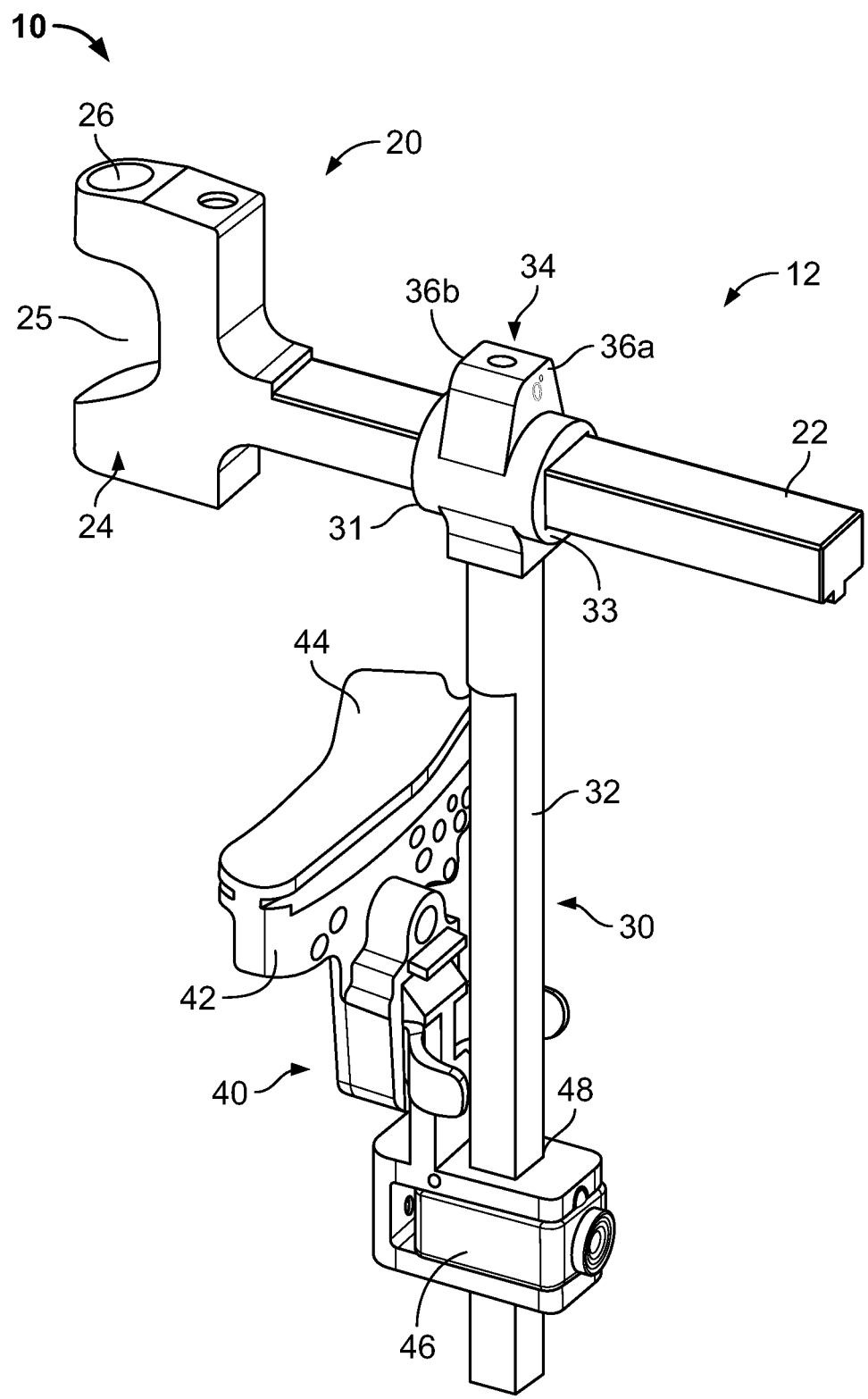
FIG. 1 is a perspective view of a tibial resection assembly according to an embodiment of the present disclosure including an IM jig and a resection guide.

Resection guide assembly 40 includes a resection guide 42 and a guide adjustment housing 46, as shown in FIG. 1. Guide 42 includes a guide surface 44 for guiding a cutting instrument, such as a bone saw. In this regard, guide surface 44 is substantially planar and may partially define a captured slot, as shown in FIG. 1, or be completely exposed. Guide housing 46 connects to resection guide 42 and includes an opening 48 that is configured to receive shaft 32 of A/P translation member 30. For example, opening 48 may have a corresponding polygonal relationship to shaft 32. Guide housing 46 is slidable in a superior-inferior direction along shaft 32 and can be secured thereto at any desired position via a locking mechanism, such as a retaining screw or ball-detent mechanism. When resection guide assembly 40 is connected to shaft of A/P translation member 30, resection guide surface 44 is perpendicular thereto.

System 10 has a first and second configuration, as depicted in FIGS. 2A-3B. One of these configurations may be selected depending on a desired posterior slope angle for a resected proximal tibia. For example, in the first configuration, shown in FIGS. 2A and 2B, A/P translation member 30 is connected to anchoring block 20 such that shaft 32 is canted toward block head 24. In other words, A/P translation member 30 is connected to anchoring block 20 such that block angle θ and first member angle $\Psi_1$ face each other and form internal angles of the intersection of axes A-A, B-B, and C-C. Axis A-A represents the axis of opening 26 which, in use, would be coaxial with an IM rod extending from a tibia and disposed within opening 26. Axis B-B represents the axis of shaft 22 of anchoring block 20 and the axis of opening 38 of A/P translation guide 30 which are coaxial when shaft 22 is disposed within opening 38. As described above, in the particular embodiment depicted, block angle θ is 1.5 degrees beyond perpendicular and first member angle $\Psi_1$ is −1.5 degrees beyond perpendicular. When IM jig 12 is in the first configuration, these angles θ, $\Psi_1$ cancel each other so that axis A-A is parallel to shaft axis C-C. As such, resection guide surface 44 of resection guide 40 attached to shaft 32 is positioned perpendicular to axis A-A such that a saw blade guided by guide surface 44 would form a posterior tibial slope of 0 degrees.

Figure 3A:
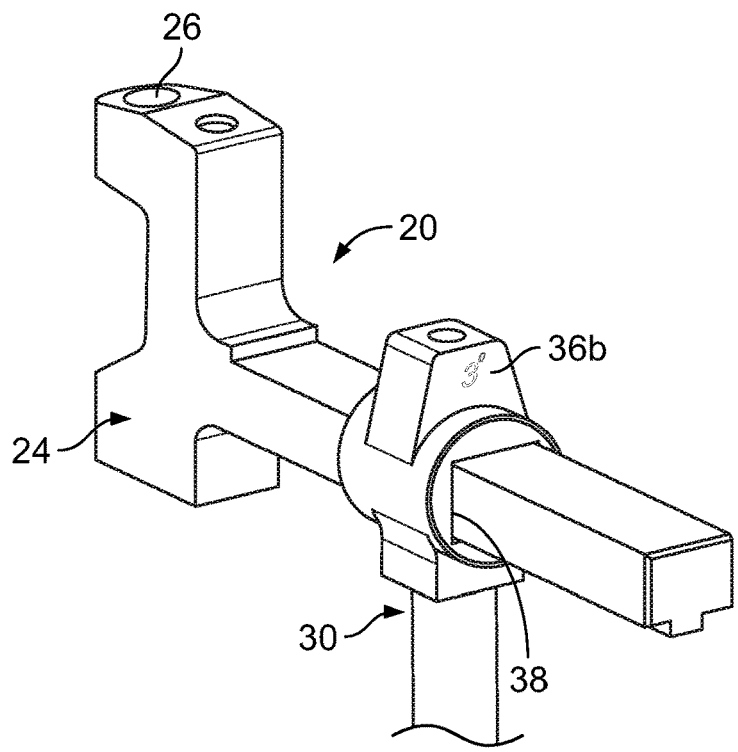
FIG. 3A is a partial perspective view of the IM jig of FIG. 1 in a second configuration.
Figure 3B:
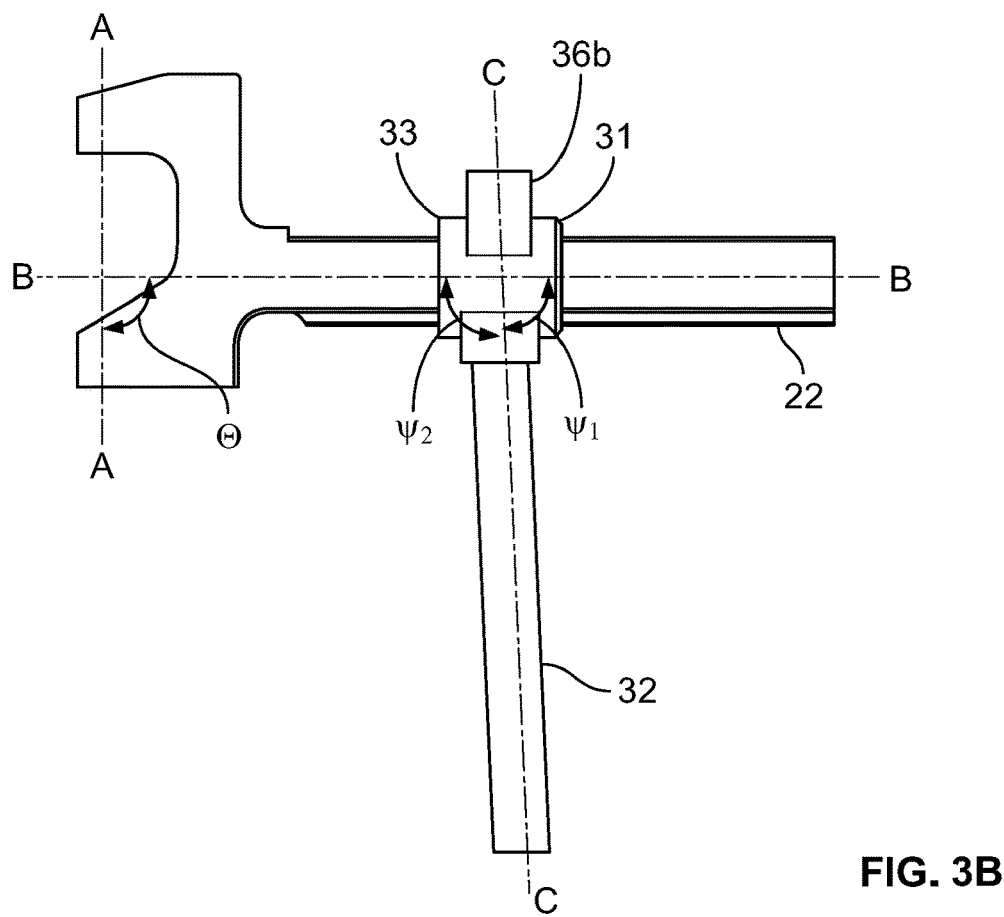
FIG. 3B is an elevational view of the IM jig of FIG. 1 in the second configuration.
Figure 4:
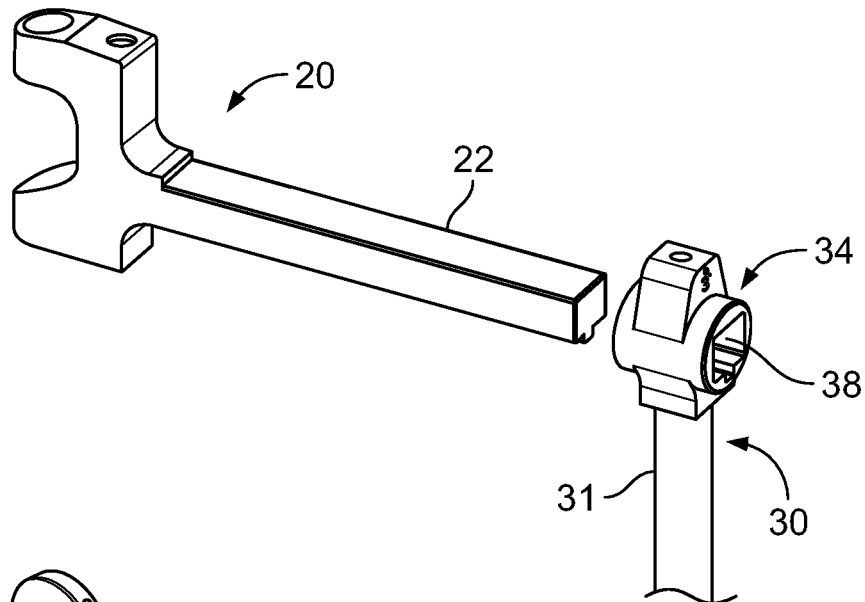
FIG. 4 is a partial exploded view of the IM jig of FIG. 1.
Figure 5:
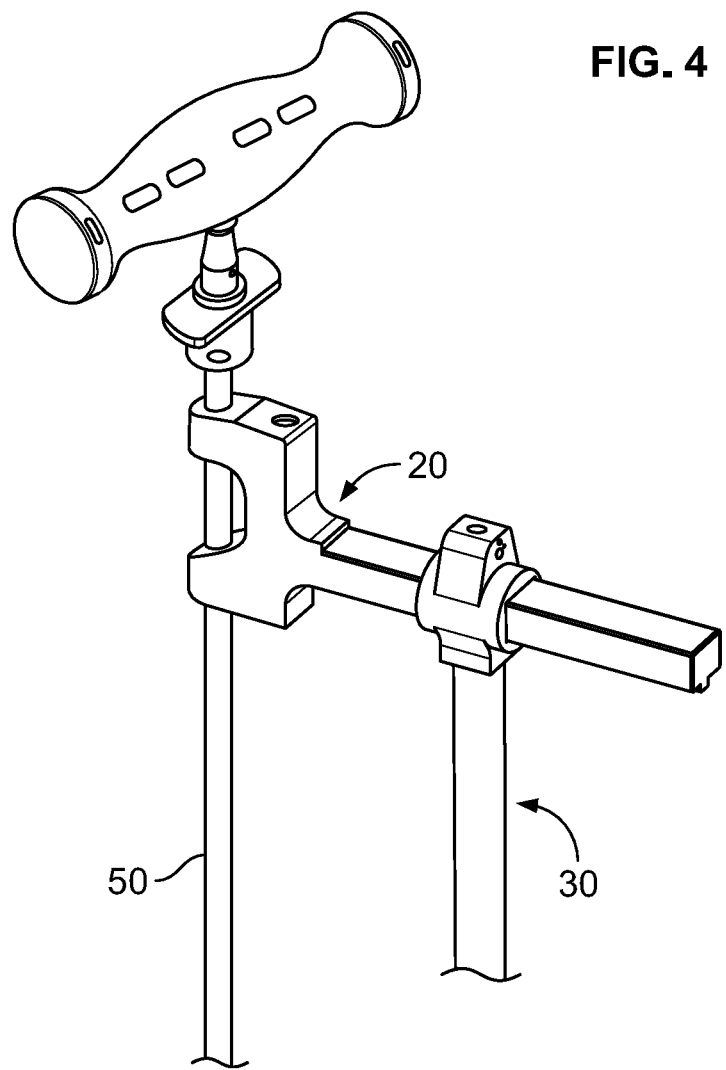
FIG. 5 is a perspective view of the IM jig of FIG. 1 connected to an IM rod.

However, in the second configuration, as shown in FIGS. 3A and 3B, A/P translation member 30 is flipped about axis C-C and connected to anchoring block 20 such that shaft 22 is canted away from block head 24 and second member angle $\Psi_2$ faces block angle θ. As described above, in the particular embodiment depicted, both angles θ and $\Psi_2$ are 1.5 degrees beyond perpendicular. In this regard, such angles θ, $\Psi_2$ add to each other so that shaft axis C-C is rotated 3 degrees relative to axis A-A. As such, resection guide surface 44 of resection guide 42 attached to shaft 32 in the second configuration is angled relative to axis A-A so that a saw blade guided by guide surface 44 would form a posterior slope of 3 degrees.

Thus, as described, in the first configuration, shaft 32 of A/P translation guide 30 is oriented relative to opening axis A-A so that a resection plane defined by resection guide 42 attached to shaft 30 intersects axis A-A at a first angle, and in the second configuration, shaft 32 of A/P translation guide 30 is orientated relative to opening axis A-A so that the resection plane defined by resection guide 42 attached to shaft 32 intersects axis A-A at a second guide angle. In the particular embodiment depicted, such angles are 0 and 3 degrees. One of these selected posterior slope angles can be achieved simply by flipping A/P member 30 about its shaft axis C-C to the appropriate orientation before connecting it to the anchoring block 20. Indicia 36a-b may be etched or otherwise located on housing 34 on opposite sides thereof to indicate to the operator the appropriate orientation for the desired posterior slope.

Although the particular embodiment depicted provides an option for applying a 0 or 3 degree posterior slope, IM jig 12 can be configured for other posterior slope angles by altering angles θ, Ψ$_1$, and Ψ$_2$. For example, IM jig can be configured to provide any combination of posterior slopes between 0 and 6 degrees based on the principles exemplified herein.

In a method of performing a proximal tibial resection, a proximal tibia is exposed and an IM rod 50 is inserted through the proximal tibia in alignment with an axis of the tibia. The operator determines an appropriate posterior slope for the proximal tibia in the conventional manner. Thus, for the embodiment depicted, if the desired posterior slope is 0 degrees, shaft 22 is slid into opening 38 from first end 31 of housing 34 so that IM jig 12 is in the first configuration with the corresponding indicia 36a facing toward the operator. Conversely, if the desired posterior slope is 3 degrees, shaft 22 is slid into opening 38 from second end 33 of housing 34 so that IM jig 12 is in the second configuration with the corresponding indicia 36b facing toward the operator.

Resection guide assembly 40 is connected to shaft 32 and moved in a superior/inferior direction to position resection guide surface 44 at an appropriate height (determined by any known methods) relative to the tibia in order to set the resection depth. Resection guide 42 may then be pinned to the tibia. Due to the selected configuration of IM jig 12, resection guide surface 44 is oriented relative to the tibia either perpendicularly or at an oblique angle. The IM rod 50 and IM jig 12 may be removed from the tibia prior to the resection. Once the IM rod 50 and IM jig 12 are removed from the bone, a saw blade is guided along surface 44 to resect the proximal tibia and form a resected surface with a designated posterior slope. Thus, for the embodiment depicted, the posterior slope of the resected tibia may be 0 or 3 degrees depending on the configuration selected.

Figure 6A:
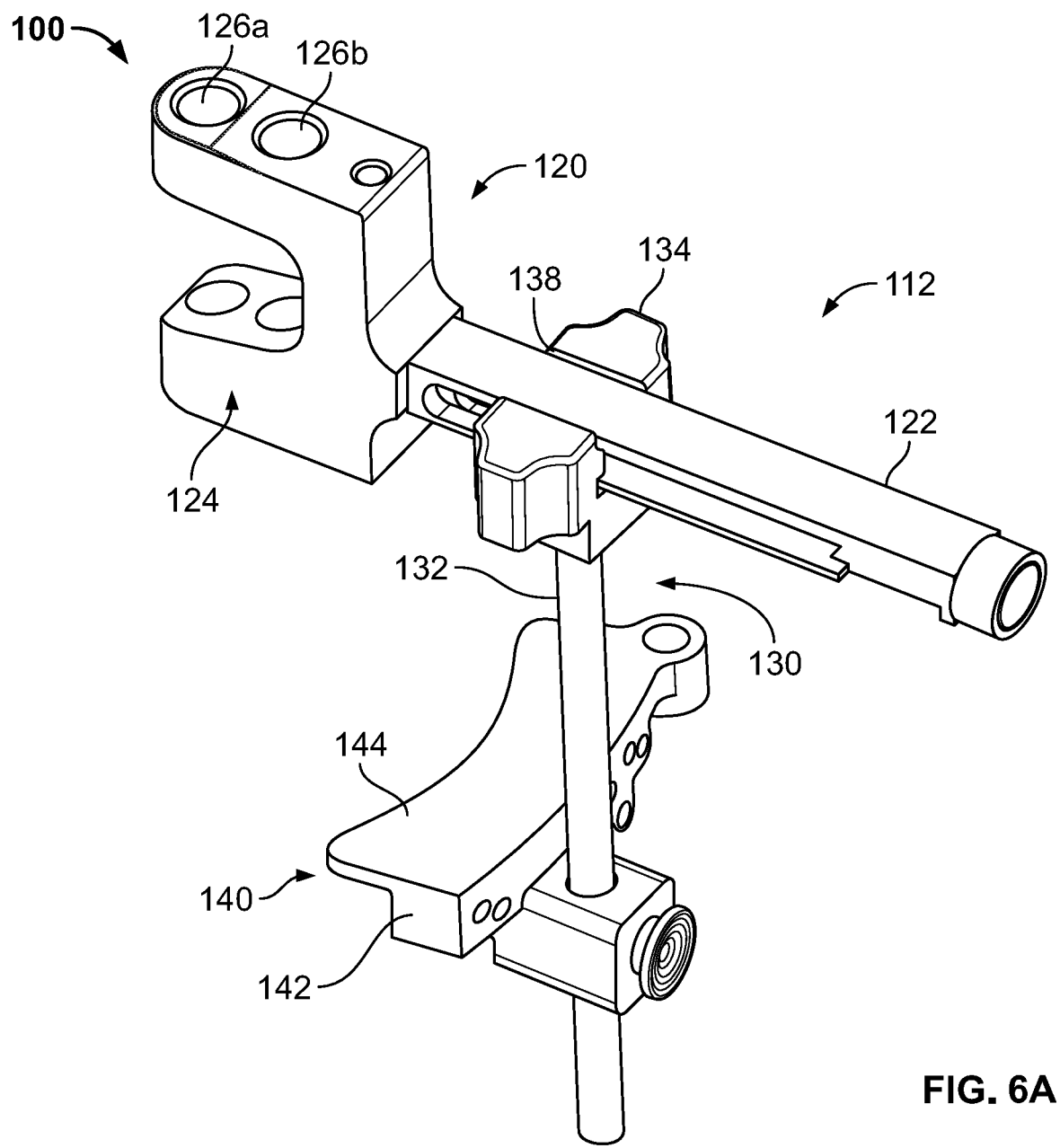
FIG. 6A is a perspective view of a tibial resection assembly according to another embodiment of the present disclosure.
Figure 6B:
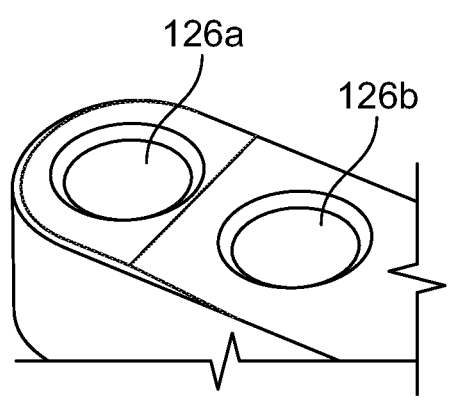
FIG. 6B is an enhanced view of an anchoring block of the tibial resection assembly of FIG. 6A.

FIGS. 6A and 6B depict a tibial resection system 100 according to another embodiment of the present disclosure. Tibial resection system 100 is similar to system 10 in that it includes an IM jig 112 and resection guide assembly 140. IM jig 112 includes an anchoring block 120 that includes a block head 124 and a shaft 122 extending from block head 124. IM jig 112 also includes an A/P translation member 130 that includes a shaft 132 and a housing 134. However, unlike system 10, shaft 132 is perpendicular to a longitudinal axis of an opening 138 in housing 134, and block head 124 includes two openings 126a-b adjacent to each other that extend entirely through block head 124 and which are each configured to receive an IM rod. Opening 138 forms an open channel and a dovetail-like arrangement, which cooperates with grooves in shaft 122 of block 120 when connected thereto.

Openings 126a-b define axes that are angled with respect to each other and with respect to shaft 122. In this regard, first and second openings 126a-b determines a posterior slope of resection guide surface. For example, first hole 126a corresponds to a 0 degree posterior slope and therefore defines an axis that is perpendicular to shaft 122 and parallel to shaft 132. However, second opening 126b corresponds to a 3 degree posterior slope and therefore defines an axis that is oblique relative to shaft 122. In this regard, when an IM rod is disposed within second opening 126b, A/P member 130 and resection guide 142 are oriented so that a saw blade guided by guide surface 144 forms a resected surface with a 3 degree posterior slope.

Although not shown, it is contemplated that block head 124 may include more than two openings with different orientations so that system 100 can be used to apply one of a plurality of different posterior slopes. For example, block head 124 may include first, second, and third openings where the first opening is configured for a 0 degree slope, the second opening is configured for a 3 degree posterior slope, and the third opening is configured for a 6 degree posterior slope. It is also contemplated to provide variable angled opening in any of the block heads of the present invention, such that the orientations can be varied by the surgeon.

In addition, variations of the above described systems are contemplated. For example, it is described above that housing 34 of A/P translation member 30 includes an opening 38 that slidably receives shaft 22. This allows resection guide assembly 40 to be moved in an A/P direction relative to the tibia. However, it is contemplated that housing 34 may not be slidably received in an opening, but may rather connect to shaft 22 in a fixed position. In this regard, housing 34 and shaft 22 may include corresponding locking mechanisms, such as a pair of magnets, a hook and latch, or some other mechanism as is understood in the art. However, such mechanism should allow A/P translation member 30 to be connected to anchoring block 20 in either the first or second configuration.

In another example, anchoring block 20 may not include block head 24. Instead, anchoring block 20 may only include shaft 22 and an opening extending through shaft 22 at an end thereof. Such opening may extend through the shaft 22 at angle θ relative to a shaft axis thereof. In this regard, head 24 is advantageous in that it is larger than shaft 22 so that an IM rod 50 disposed within opening 26 is well engaged by block 20 along its length to prevent block 20 from wobbling relative to IM rod 50. However, head 24 is not essential.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A resection guide system for resecting an end of bone, comprising:
   an anchoring block having a head and an elongate shaft immovably fixed to the head, the head having an opening extending therethrough at one end thereof, the opening being sized to receive an intramedullary rod therein, the opening defining a longitudinal axis;
   a translation member having a housing and a shaft monolithically formed with and extending from the housing, the housing of the translation member being engageable to the shaft of the anchoring block in a first configuration in which the shaft of the translation member is oriented at a first angle relative to the longitudinal axis of the opening and a second configuration in which the shaft of the translation member is oriented at a second angle relative to the longitudinal axis of the opening; and
   a resection guide assembly connected to the shaft of the translation member and having a resection guide surface adapted to guide a cutting instrument along a plane defined by the resection guide surface.

2. The system of claim 1, wherein the shaft of the anchoring block has a shaft axis that intersects the longitudinal axis of the opening at an obtuse angle.

3. The system of claim 2, wherein the housing of the translation member has an opening extending therethrough from a first end to a second end thereof, the opening of the housing being configured to receive the shaft of the anchoring block.

4. The system of claim 3, wherein the head has a cross-sectional dimension greater than the shaft and the opening extends through the head, and wherein in the first configuration the shaft of the anchoring block extends through the opening of the housing so that the first end of the housing faces the head of the anchoring block, and in the second configuration the shaft of the anchoring block extends through the opening of the translation member so that the second end of the housing faces the head of the anchoring block.

5. The system of claim 4, wherein the shaft of the translation member is canted relative to the housing.

6. The system of claim 5, wherein in the first configuration the shaft of the anchoring block is received in the opening of the housing so that the shaft of the translation member is canted toward the head of the anchoring block, and in the second configuration the shaft of the anchoring block is received in the opening of the housing so that the shaft of the translation member is canted away from the head of the anchoring block.

7. The system of claim 1, wherein the first angle is 0 degrees such that the longitudinal axis is parallel to the shaft of the translation member, and the second angle is 3 degrees.

8. The system of claim 7, wherein the plane defined by the resection guide surface is perpendicular to a shaft axis of the translation member.

9. A resection guide system for resecting an end of a tibia, comprising:
an anchoring block having a shaft and opening extending through the shaft at an end thereof, the opening being configured to receive an IM rod extending from the tibia;
a translation member having a housing and a shaft extending from the housing; and
a resection guide assembly having a resection guide surface, the resection guide assembly being connectable to the shaft of the translation member,
wherein the housing of the translation member is configured to connect to the anchoring block in a first configuration such that the resection guide surface of the resection guide assembly is positioned in a first orientation relative to the tibia when the IM rod is received within the opening and in a second configuration such that the resection guide surface of the resection guide assembly is positioned in a second orientation relative to the tibia, and
wherein in the first configuration a first end of the housing faces the anchoring block, and in the second configuration a second end of the housing faces the anchoring block.

10. The system of claim 9, wherein the housing defines an opening extending therethrough from the first end to the second end thereof, the opening defining a housing axis and being configured to receive the shaft of the anchoring block.

11. The system of claim 10, wherein the shaft of the translation member is canted relative to the housing such that a shaft axis of the translation member intersects the housing axis at an oblique angle.

12. The system of claim 11, wherein the anchoring block includes a head at an end thereof, the head having a cross-sectional dimension greater than the shaft and the opening extending through the head, and wherein the shaft of the anchoring block is canted relative to the head such that a shaft axis of the anchoring block intersects a longitudinal axis of the opening of the head at an oblique angle.

13. The system of claim 9, wherein the resection guide surface is perpendicular to the shaft of the translation member when the resection guide assembly is connected thereto.

14. A method of resecting a proximal tibia, comprising:
mounting an anchoring block onto an IM rod extending from the proximal tibia;
selecting one of a first and second posterior slope angle for application to the proximal tibia;
if the first posterior slope angle is selected, mounting a translation member carrying a resection guide assembly to the anchoring block in a first configuration such that a shaft of the anchoring block engages a housing of the translation member and a first end of the housing faces the tibia, the resection guide assembly having a resection guide surface disposed in a first orientation relative to the tibia;
if the second posterior slope angle is selected, mounting the translation member carrying the resection guide assembly to the anchoring block in a second configuration such that the shaft engages the housing and a second end of the housing faces the tibia, the resection guide surface being disposed in a second orientation relative to the tibia; and
resecting the tibia along the resection guide surface of the resection guide assembly.

15. The method of claim 14, wherein in the second configuration a shaft of the translation member is canted away from the tibia, the resection guide assembly being connected to the shaft of the translation member.

16. The method of claim 14, wherein mounting the anchoring block to the IM rod includes inserting the IM rod into an opening extending through a head of the anchoring block.

17. The method of claim 14, wherein mounting the translation member to the anchoring block in the first configuration includes inserting the shaft of the anchoring block through an opening in the housing of the translation member from the first end of the housing to the second end of the housing.

18. The method of claim 17, wherein mounting the translation member to the anchoring block in the second configuration includes inserting the shaft of the anchoring block through the opening in the housing of the translation member from the second end of the housing to the first end of the housing.

* * * * *